United States Patent [19]

Nakagawa et al.

[11] 4,026,897
[45] May 31, 1977

[54] 5-[1-HYDROXY-2-(SUBSTITUTED-AMINO)-]ALKYL-8-HYDROXYCARBOSTYRIL DERIVATIVES

[75] Inventors: Kazuyuki Nakagawa, Tokushima; Shiro Yoshizaki, Naruto; Kaoru Tanimura, Tokushima; Shigeharu Tamada, Tokushima, all of Japan

[73] Assignee: Otsuka Pharmaceutical Company, Tokyo, Japan

[22] Filed: Dec. 26, 1974

[21] Appl. No.: 536,515

[30] Foreign Application Priority Data

May 22, 1974  Japan .................. 49-58315
May 22, 1974  Japan .................. 49-58317
June 13, 1974 Japan .................. 49-67823
Nov. 11, 1974 Japan .................. 49-130717
Nov. 11, 1974 Japan .................. 49-130718
Nov. 11, 1974 Japan .................. 49-130727
Dec. 4, 1974  Japan .................. 49-140339

[52] U.S. Cl. .................. 260/288 R; 260/247.2 A; 260/268 BQ; 260/289 R; 424/248.54; 424/250; 424/258

[51] Int. Cl.$^2$ ............. C07D 215/26; C07D 215/22

[58] Field of Search ... 260/288 CE, 288 R, 247.2 A, 260/268 BQ

[56] References Cited

UNITED STATES PATENTS 3,444,173  5/1969  Goldman .................. 260/288 CE
3,555,030  1/1971  Loev et al. ................ 260/289 R

FOREIGN PATENTS OR APPLICATIONS 2,261,506  6/1973  Germany ................. 260/268 R

OTHER PUBLICATIONS

Morrison et al.; Organic Chemistry, (1969), p. 666.
Chodnekar et al.; J. Med. Chem., vol. 15, pp. 49–57 (1972).
Morrison et al.; Org. Chem. (1969) p. 866.
Beist et al.; Arch. int. Pharmacodyn. vol. 209, pp. 227–236 (1974).
Cantarelli et al.; Chem. Abs. vol. 67, 2958a (1967).
Chem. Abs. vol. 62:16212e (Abst. of Neth. Appl. 6,405,107) 1965.
Chem. Abs. vol. 81:3968e (1974).

Primary Examiner—Donald G. Daus
Assistant Examiner—Mary Vaughn
Attorney, Agent, or Firm—Sughrue, Rothwell, Mion, Zinn & Macpeak

[57] ABSTRACT

5-[1-Hydroxy-2-(substituted-amino)]alkyl -8-hydroxycarbostyril derivatives represented by the formula (I)

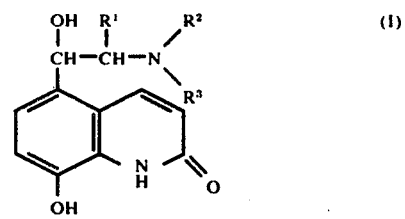

wherein $R^1$ represents an alkyl group having 1 to 4 carbon atoms and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, the pharmaceutically acceptable acid addition salts thereof, and a process for preparing the same.

8 Claims, No Drawings

5-[1-HYDROXY-2-(SUBSTITUTED-AMINO)]ALKYL-8-HYDROXYCARBOSTYRIL DERIVATIVES

BACKGROUND OF THE INVENTION

1. Field of the Invention

This invention relates to a novel carbostyril derivative and a process for preparing the same. More particularly, this invention relates to a novel 5-[1-hydroxy-2-(substituted-amino)]alkyl -8-hydroxycarbostyril derivatives and the pharmaceutically acceptable acid addition salts thereof, and a process for preparing the same.

2. Description of the Prior Art

It is well known that certain carbostyril derivatives exhibit useful pharmaceutical activities. Representative compounds of this type have been disclosed in *Journal of Medical Chemistry*, Vol. 15, No. 3, pp. 260 – 266 (1972), Japanese Patent Publication No. 38789/1971 and *Chemical Abstracts*, 62, 16212e (1965), etc. However, these prior art references do not teach that the compounds having a [1-hydroxy-2-(substituted-amino)]-alkyl group at the 5-position of the carbostyril moiety possess an excellent β-adreno-receptor stimulating activity.

It has now been found that 8-hydroxycarbostyril derivatives having a [1-hydroxy-2-(substituted-amino)-]alkyl group at the 5-position of the carbostyril moiety and the pharmaceutically acceptable acid addition salts thereof possess a β-adreno-receptor stimulating activity and, therefore, are useful as a therapeutic agent such as a bronchodilator, a peripheral vasodilator, an antihypertensive agent and the like, particularly for treating bronchial asthma.

SUMMARY OF THE INVENTION

An object of the present invention is to provide novel 5-[(1-hydroxy-2-substituted-amino)]alkyl -8-hydroxycarbostyril derivatives represented by the formula (I)

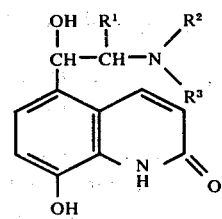

wherein $R^1$ represents an alkyl group having 1 to 4 carbon atoms and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms.

Another object of this invention is to provide a process for preparing the above 5- [1-hydroxy-2-(substituted-amino)]alkyl -8-hydroxycarbostyril derivatives represented by the formula (I)

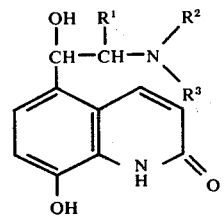

wherein $R^1$ represents an alkyl group having 1 to 4 carbon atoms and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, which comprises the steps of:

1. reacting 8-hydroxycarbostyril of the formula (VI)

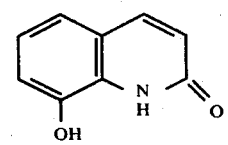

with an α-halo-alkanoic acid halide of the formula (V)

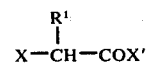

wherein $R^1$ represents an alkyl group having 1 to 4 carbon atoms, and X and X' may be the same or different and each represents a halogen atom, in the presence or absence of a solvent and in the presence of a Lewis acid catalyst, to obtain a 5-(α-haloalkanoyl)-8-hydroxycarbostyril derivative of the formula (IV)

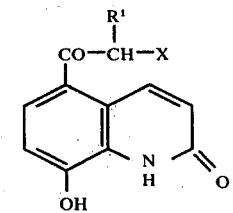

wherein R and X are as defined above, 2. reacting the 5-(α-haloalkanoyl)-8-hydroxycarbostyril thus obtained with an amine of the formula (III)

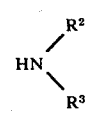

wherein $R^2$ and $R^3$ are as defined above, in the presence or absence of a solvent, to obtain 5-(α-substituted-aminoalkanoyl)-8-hydroxycarbostyril of the formula (II)

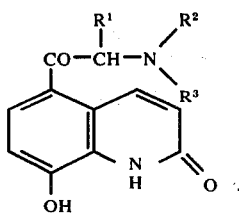

wherein $R^1$, $R^2$ and $R^3$ are as defined above, and 3. reducing the 5-(α-substituted-aminoalkanoyl)-8-hydroxycarbostyril of the formula (II) with hydrogen in the presence of a hydrogenation catalyst or with a reducing agent.

DETAILED DESCRIPTION OF THE INVENTION

The 5-[1-hydroxy-2-(substituted-amino)]alkyl -8-hydroxycarbostyril derivatives of the formula (I) and the acid addition salts thereof exhibit a β-adrenoreceptor stimulating activity and, therefore, are useful as a bronchodilator, a peripheral vasodilator or an antihypertensive agent.

The term "alkyl" as used herein means a straight or branched chain alkyl group. Suitable examples of such groups having 1 to 4 carbon atoms include, for example, methyl, ethyl, propyl, isopropyl, butyl, sec-butyl, tert-butyl groups and the like.

The term "aralkyl" as used herein means an aralkyl group containing a straight or branched chain alkyl moiety having 1 to 4 carbon atoms, for example, a benzyl, α-methylbenzyl, α,α-dimethylbenzyl, phenethyl, α,α-dimethylphenethyl group and the like.

The term "cycloalkyl" as used herein means a cycloalkyl group having 4 to 6 carbon atoms, for example, a cyclobutyl, cyclopentyl, cyclohexyl group and the like.

The term "5- or 6-membered substituted or unsubstituted heterocyclic ring" as used herein means a heterocyclic group containing 1 or 2 nitrogen, oxygen or sulfur atoms as hetero atoms such as a pyrrolidino, pyrrolidinyl, piperidino, piperidinyl, morpholino, morpholinyl, piperazino, piperazinyl or a like group which can be unsubstituted or substituted with an alkyl group having 1 to 4 carbon atoms, such as a methyl, ethyl, iso-propyl, tert-butyl group and the like, for example, a 2-methylpiperidino, 3-methylpiperidino, N-methylpiperazino group and the like.

The term "halogen" as used herein includes fluorine, chlorine, bromine and iodine, preferably, chlorine and bromine.

According to the present invention, the compounds represented by the formula (I) can be prepared by 1. reacting 8-hydroxycarbostyril of the formula (VI)

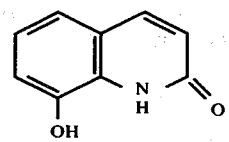

with an α-halo-alkanoic acid halide of the formula (V)

wherein $R^1$ represents an alkyl group having 1 to 4 carbon atoms; and X and X', which may be the same or different, each represents a halogen atom, in the presence of a Lewis acid catalyst, to obtain a 5-(α-haloalkanoyl)-8-hydroxycarbostyril derivative having the formula (IV)

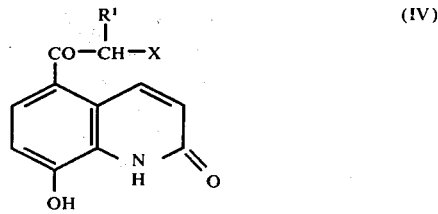

wherein $R^1$ and X are as defined above, 2. reacting the resulting 5-(α-haloalkanoyl)-8-hydroxycarbostyril derivative of the formula (IV) with an amine of the formula (III)

wherein $R^2$ and $R^3$ are as defined above, to obtain a 5-(α-substituted-aminoalkanoyl)-8-hydroxycarbostyril derivative having the formula (II)

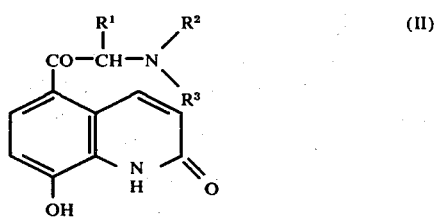

wherein $R^1$, $R^2$ and $R^3$ are as defined above, and 3. reducing the resulting 5-(α-substituted-aminoalkanoyl)-8-hydroxycarbostyril derivative of the formula (II) with a reducing agent.

The compounds of the formulas (IV), (II) and (I) described above are all novel compounds and the process for the preparation of the compounds of the formula (I) and intermediate compounds (II) and (IV) is described in detail below.

The 8-hydroxycarbostyril of the formula (VI) used as a starting material of the present invention is a known compound, and can easily be prepared, for example, by the method as described in George R. Pettit et al, J. Org. Chem., 33, 1089 (1968).

The α-halo-alkanoic acid halide of the formula (V) which can be used in this invention includes α-chloropropionyl chloride, α-bromopropionyl chloride, α-chlorobutyryl chloride, α-bromobutyryl chloride, α-bromobutyryl bromide, α-chlorovaleryl chloride and the like.

The reaction between the 8-hydroxycarbostyril of the formula (VI) and the α-halo-alkanoic acid halide of the formula (V) can be conducted using a Lewis acid as a catalyst, for example, aluminum chloride, aluminum bromide, ferric chloride, stannic chloride, titanium chloride, boron trifluoride, with aluminum chloride being preferable. The Lewis acid can be used in an amount of about 2 to about 10 moles, preferably 3 to 6 moles per mole of the 8-hydroxycarbostyril of the formula (VI). The α-halo-alkanoic acid halide of the formula (V) is used in an equimolar amount to a large excess relative to the 8-hydroxycarbostyril of the formula (VI) but generally in an amount of about 2 to about 20 moles, preferably 2 to 10 moles, per mole of the 8-hydroxycarbostyril of the formula (VI). The reaction can be carried out in the absence or presence of an appropriate solvent such as carbon disulfide, nitrobenzene and the like, preferably carbon disulfide, in a volume of about 0.5 to about 20, preferably 2 to 10 times the volume of the reactants, and in the presence of the above enumerated catalyst under anhydrous conditions at the room temperature (about 20° to 30° C) to about 150° C, preferably room temperature to 80° C, for a period of 1 to 20, preferably 1 to 10 hours.

The amines of the formula (III) which can be used in the reaction with the 5-(α-haloalkanoyl)-8-hydroxycarbostyril of the formula (IV) include alkylamines, for example, methylamine, ethylamine, n-propylamine, isopropylamine, n-butylamine, sec-butylamine tert-butylamine and the like; cycloalkylamines, for example, cyclobutylamine, cyclopentylamine, cyclohexylamine; aralkylamines, for example, benzylamine, α-methylbenzylamine, α,α-dimethylbenzylamine, phenethylamine, α,α-dimethylphenethylamine and the like; and substituted or unsubstituted heterocyclic amines, for example, pyrrolidine, piperidine, morpholine, piperazine, 2-methylpiperidine, 3-methylpiperidine N-methylpiperazine and the like.

This reaction between the amine of the formula (III) and and the 5-(α-haloalkanoyl)-8-hydroxycarbostyril of the formula (IV) can be effected using the amine of the formula (IV) in an equimolar amount to a large excess, preferably about 2 to about 10 moles per mole of the compound of the formula (IV), at a temperature of from room temperature to the refluxing temperature of the reaction system, preferably at a temperature of from 40° to 100° C at about atmospheric pressure to about 10 atmospheres in an appropriate solvent or using the amine of the formula (III) per se as a solvent. Suitable solvents which can be used in this reaction include lower alcohols such as methanol, ethanol, propanols and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferred.

The subsequent reduction of the thus obtained 5-(α-substituted-aminoalkanoyl)-8-hydroxycarbostyril of the formula (II) can be conducted by a conventional reduction using a reducing agent such as lithium aluminum hydride, sodium borohydride and the like, or a conventional catalytic reduction with hydrogen in the presence of a hydrogenation catalyst such as palladium black, palladium-on-carbon, Raney nickel, platinum black, platinum oxide and the like.

The above reducing agent can be used in an amount of from about 2 to about 10 moles, preferably 2 to 5 moles, per mole of the carbostyril compound of the formula (II) in a solvent while cooling under atmospheric pressure at a temperature of from about 0° to about 100° C, preferably 20° to 50° C. When sodium borohydride is used as the reducing agent, the solvent is preferably water or alcohols such as methanol, ethanol and the like, and when lithium aluminum hydride is used as the reducing agent, the solvent is preferably a non-aqueous solvent such as anhydrous diethyl ether, ethyl acetate, tetrahydrofuran and the like.

The catalytic reduction can be carried out with hydrogen using the above hydrogenation catalyst in an amount of from about 0.05 to about 1 mole, preferably from 0.1 to 0.5 mole, per mole of the carbostyril compound of the formula (II) in a solvent, for example, water or an alcohol such as methanol, ethanol or isopropanol under a hydrogen atmosphere at a pressure of from about atmospheric pressure to about 100 atmospheres, preferably from atmospheric pressure to 50 atmospheres, at a temperature of from room temperature to about 150° C, preferably room temperature to 120° C, advantageously with agitating the reduction system. It is advantageous to carry out the above catalytic reduction at a temperature higher than about 50° C at atmospheric pressure or at a temperature higher than room temperature under pressure.

The compounds of the present invention represented by the formula (I) wherein $R^2$ and $R^3$ represent hydrogen atoms can also be prepared from the compounds of the formula (II) wherein either $R^2$ or $R^3$ represents a benzyl group or an α-methylbenzyl group. The above benzyl or α-methylbenzyl group can easily be split off during the catalytic reduction to produce the compounds of the present invention wherein $R^2$ and $R^3$ are hydrogen atoms.

Alternatively, the carbostyril derivatives represented by the formula (I) can be prepared from the corresponding 5-[1-hydroxy-2-(substituted-amino)]alkyl-8-hydroxy-3,4-dihydrocarbostyril of the formula (VII)

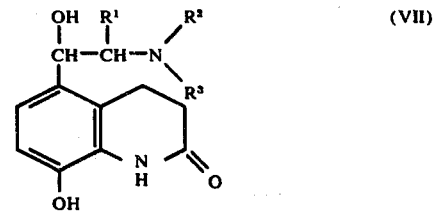

by dehydrogenation. The dehydrogenation can be carried out by any conventional procedure known to be useful for liberating a hydrogen atom from the 3- and the 4-positions of the carbostyril moiety, for example, by (1) a procedure using a dehydrogenation agent such as chloranil (tetrachloro-1,4-benzoquinone), dichlorodicyano-1,4-benzoquinone and the like, (2) a procedure using a metal catalyst for dehydrogenation such as palladium black, platinum black, platinum oxide, Raney nickel and the like, or (3) a procedure using sulfur, selenium dioxide and the like. However, for ease of operations, the procedure (1) or (2) above can conveniently be used in the present invention.

Further, the carbostyril derivatives represented by the formula (I) can be prepared by dealkylating a 5-[1-hydroxy-2-(substituted-amino)]alkyl-8-alkoxycarbostyril derivative of the formula (VIII)

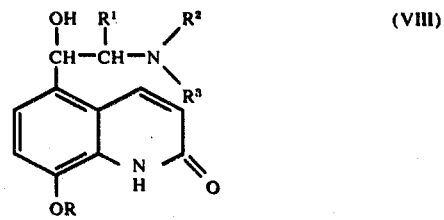

with a hydrohalic acid as disclosed in copending application, U.S. patent application Ser. No. 536,703, filed Dec. 26, 1974 filed simultaneously herewith.

The dehydrogenation can be generally carried out in a solvent, for example, aromatic hydrocarbons such as benzene, toluene, xylene, phenetol, chlorobenzene and the like, lower alcohols such as methanol, ethanol, isopropanol, tert-butanol and the like, ethers such as dioxane and the like, ketones such as acetone, water, acetic acid, etc., in the presence of the dehydrogenation agent or the dehydrogenation metal catalyst as enumerated above, at a temperature of from room temperature to the refluxing temperature of the dehydrogenation reaction system, preferably at the refluxing temperature for a period of from about 10 to about 30 hours. The dehydrogenation agent is generally used in an amount of about 1 to about 5 moles per mole of the 3,4-dihydrocarbostyril of the formula (VII), and the metal catalyst is generally used in an amount of about 0.5 to about 3 moles per mole of the 3,4-dihydrocarbostyril of the formula (VII).

The 5-[1-hydroxy-2-(substituted-amino)]alkyl-8-hydroxycarbostyril derivatives of the formula (I) as obtained above are basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc., or organic acids such as oxalic acid, maleic acid, fumaric acid, malic acid, tartaric acid, citric acid, ascorbic acid, etc. These acid addition salts can easily be prepared by well known procedures, for example, by adding an equimolar to an excess amount of the acid to a solution of the compound of the formula (I) dissolved in an appropriate organic solvent such as methanol, ethanol, isopropanol, acetone and the like.

Both the free bases of the compounds of the formula (I) and the acid addition salts thereof are novel compounds and exhibit a stimulating activity on $\beta$-adrenoreceptor, and therefore, are very useful as pharmaceuticals such as a bronchodilator, a peripheral vasodilator, an antihypertensive agent and the like, particularly for treating bronchial asthma. As is apparent to one skilled in the art, the compounds of the present invention contain two asymmetrical centers and, therefore, can be present in four optically active forms.

Particularly preferred compounds of the formula (I) are the following basic compounds and their hydrochlorides, sulfates, phosphates, maleates, fumarates and oxalates.

5-(1-Hydroxy-2-isopropylamino)butyl-8-hydroxycarbostyril
5-(1-Hydroxy-2-sec-butylamino)butyl-8-hydroxycarbostyril
5-(1-Hydroxy-2-isopropylamino)propyl-8-hydroxycarbostyril
5-(1-Hydroxy-2-tert-butylamino)propyl-8-hydroxycarbostyril
5-(1-Hydroxy-2-ethylamino)butyl-8-hydroxycarbostyril
5-[1-Hydroxy-2-(2-phenethylamino)]butyl-8-hydroxycarbostyril The present invention is further illustrated in greater detail by reference to the following Examples, but they are given for illustrative purposes only and are not to be construed as limiting the scope of the invention. Unless otherwise indicated, all parts, percents, ratios and the like are by weight.

EXAMPLE 1

50 g of $\alpha$-bromobutyric acid bromide (V), 50 g of anhydrous aluminum chloride and 400 ml of carbon disulfide were added to 20 g of 8-hydroxycarbostyril (VI). The resulting mixture was heated at a temperature of 50° C for 13 hours and the carbon disulfide layer was removed by decantation. Crushed ice was added to the residue to crystallize the product, and the crystals thus formed were filtered, washed with water and then recrystallized from methanol to obtain 27 g of 5-($\alpha$-bromobutyryl)-8-hydroxycarbostyril (VI) having a melting point of 218°–219° C (with coloring and decomposition).

EXAMPLE 2

25 g of $\alpha$-bromobutyric acid chloride (V) and 25 g of anhydrous aluminum chloride were added to 10 g of 8-hydroxycarbostyril (VI), and the resulting mixture was heated at a temperature of 70° C for 4 hours while thoroughly stirring. After crushed ice was added to the mixture to crystallize the product, the crystals thus formed were filtered, washed with water and then recrystallized from methanol to obtain 12.6 g of 5-($\alpha$-bromobutyryl)-8-hydroxycarbostyril (VI) having a melting point of 218°–219° C (with coloring and decomposition).

EXAMPLE 3

25 g of $\alpha$-bromobutyric acid bromide (V) and 100 ml of nitrobenzene were added to 10 g of 8-hydroxycarbostyril (VI), and 25 g of anhydrous aluminum chloride was added to the resulting solution under cooling. The mixture was heated at a temperature of 70° C for 10 hours followed by pouring onto crushed ice. The precipitated crystals were filtered, washed with water and recrystallized from methanol to obtain 11.2 g of 5-($\alpha$-bromobutyryl)-8-hydroxycarbostyril (IV) having a melting point of 217°–218.5° C (with coloring and decomposition).

EXAMPLE 4

200 ml of sec-butylamine (III) was added to 10 g of 5-($\alpha$-bromobutyryl)-8-hydroxycarbostyril (IV) obtained as described in Examples 1 to 3, and the resulting mixture was heated at a temperature of 60° C for 20 hours followed by concentration to dryness. Crystals which formed upon addition of water were filtered, dissolved in 50 ml of ethanol, and the resulting solution was adjusted to a pH of 1 with concentrated hydrochloric acid. The precipitated crystals were filtered and recrystallized from methanol to obtain 8.3 g of 5-($\alpha$-sec-butylaminobutyryl)-8-hydroxycarbostyril (II) hydrochloride having a melting point of 212°–214° C (with coloring and decomposition).

EXAMPLE 5

10 ml of iso-propylamine (III) and 50 ml of methanol were added to 5 g of the 5-($\alpha$-bromobutyryl)-8-hydroxycarbostyril (IV) obtained in Examples 1 to 3. The resulting mixture was heated under refluxing for 6 hours followed by concentration to dryness. The reaction product was further worked up in the same manner as described in Example 1 to obtain 4.2 g of a methanol solvate of 5-($\alpha$-iso-propylaminobutyryl)-8-hydroxycarbostyril (II) having a melting point of 136°–137° C (with foaming and decomposition).

EXAMPLE 6

50 g of α-bromobutyric acid bromide (V), 50 g of anhydrous aluminum chloride and 400 ml of carbon disulfide were added to 20 g of 8-hydroxycarbostyril (VI). The resulting mixture was heated at a temperature of 50° C for 13 hours and the carbon disulfide layer was removed by decantation. Crushed ice was added to the residue, and the precipitated crystals were filtered, washed with water and recrystallized from methanol to obtain 27 g of 5-(α-bromobutyryl)-8-hydroxycarbostyril (IV) having a melting point of 218°–219° C (with coloring and decomposition). To 5 g of the thus obtained 5-(α-bromobutyryl)-8-hydroxycarbostyril (IV) was added 100 ml of iso-propylamine (III), and the mixture was heated at a temperature of 50° C for 4 hours followed by concentration to dryness. Crystals which formed upon addition of water were filtered, washed with water and then recrystallized from methanol to obtain 4.6 g of a methanol solvate of 5-(α-iso-propylaminobutyryl)-8-hydroxycarbostyril (II) having a melting point of 136°–137° C (with foaming and decomposition).

EXAMPLE 7

25 g of 2-phenethylamine (III) was added to 5 g of the (α-bromobutyryl)-8-hydroxycarbostyril (IV) prepared as in Example 1, 2 or 3, and the mixture was stirred at a temperature of 30° C for 8 hours. A mixture of diethyl ether and petroleum ether was added to the reaction mixture and the precipitated material was dissolved in dilute hydrochloric acid to remove any insoluble material. The hydrochloric acid layer was concentrated and the precipitate was filtered and recrystallized from ethanol to obtain 5.3 g of a material having a melting point of 200°–201° C (with coloring and decomposition). The material thus obtained was confirmed by NMR and IR spectral analyses and elemental analysis to be 5-[α-(2-phenethylamino)-butyryl]-8-hydroxycarbostyril (II) hyrochloride dihydrate.

EXAMPLE 8

5 ml of morpholine (III) was added to 5 g of the 5-(α-bromobutyryl)-8-hydroxycarbostyril (IV) prepared as in Examples 1 to 3, and the mixture was allowed to react at a temperature of 40° C for 4 hours with stirring. The reaction mixture was then concentrated under reduced pressure, and 100 ml of water was added to the resulting residue. The mixture was stirred and filtered followed by concentration of the filtrate mother liquor under reduced pressure. The residue was dissolved in acetone and the solution was filtered to remove any insoluble material. The filtrate was then concentrated under reduced pressure, adjusted to a pH of 2 – 3 with concentrated hydrochloric acid, and the precipitate formed upon ice-cooling was recrystallized from ethanol to obtain 2.1 g of white amorphous 5-(α-morpholinobutyryl)-8-hydroxycarbostyril (II) hydrochloride monohydrate having a melting point of 179°–182° C (with decomposition). The product thus obtained was confirmed by IR and NMR spectral analyses and elemental analysis.

EXAMPLE 9

40 ml of methanol was added to 2 g of the 5-(α-isopropylaminobutyryl)-8-hydroxycarbostyril (II) obtained as in Example 5 or 6, and 2.5 g of sodium borohydride was added portionwise to the resulting solution while stirring under ice-cooling followed by further stirring at room temperature for an additional hour. Concentrated hydrochloric acid was added to the reaction mixture to adjust the pH to 1, and the mixture was then concentrated to dryness. The precipitates were washed with acetone, dissolved in water, and then adjusted to a pH of 8 with aqueous sodium hydroxide to precipitate crystals. The resulting crystals were collected by filtration and recrystallized from ethanol to obtain 1.8 g of 5-(1-hydroxy-2-iso-propylamino)-butyl-8-hydroxycarbostyril (I) monohydrate having a melting point of 141°–142° C (with coloring and decomposition).

EXAMPLE 10

30 ml of methanol was added to 1.5 g of the 5-(α-sec-butylaminobutyryl)-8-hydroxycarbostyril (II) prepared as in Example 4, and 1.5 g of sodium borohydride was added portionwise to the resulting solution while stirring under ice-cooling. The stirring was further continued at room temperature for an additional hour. The reaction mixture was then adjusted to a pH of 1 with concentrated hydrochloric acid followed by concentration to dryness. The precipitates were filtered, washed with acetone, dissolved in water and then adjusted to a pH of 8 with aqeous sodium hydroxide. The precipitated crystals were filtered, washed with water and again dissolved in diluted hydrochloric acid. The resulting solution was concentrated to dryness, and the precipitates were recrystallized from ethanol to obtain 1.3 g of 5-(1-hydroxy-2-sec-butylamino)butyl-8-hydroxycarbostyril (I) hydrochloride monohydrate having a melting point of 182°–183° C (with foaming and decomposition).

EXAMPLE 11

20 ml of tetrahydrofuran was added to 1 g of the 5-(α-isopropylaminobutyryl)-8-hydroxycarbostyril (II) hydrochloride obtained as in Example 5 or 6, and the resulting mixture was added dropwise to a suspension of 0.12 g of lithium aluminum hydride in 10 ml of tetrahydrofuran while stirring at room temperature. After completion of the addition, a small amount of water was added to the reaction mixture to decompose any excess of lithium aluminum hydride. The reaction mixture was then poured into 50 ml of ice-water and the aqueous layer of the resulting solution was separated and concentrated to dryness. The precipitated crystals were filtered, washed with acetone and dissolved in water. The solution was adjusted to a pH of 8 with aqueous sodium hydroxide to precipitate crystals which were then filtered and recrystallized from ethanol to obtain 0.8 g of 5-(1-hydroxy-2-isopropylamino)butyl-8-hydroxy-carbostyril (I) monohydrate having a melting point of 141°–142° C (with coloring and decomposition).

EXAMPLE 12

1.5 g of the free base of the 5-[α-(2-phenethylamino)-butyryl]-8-hydroxycarbostyril (II) prepared as in Example 7 was dissolved in 150 ml of methanol, and 2 g of sodium borohydride was added slowly to the solution under ice-water cooling while stirring followed by continuing the stirring at room temperature for an additional hour. The resulting mixture was then adjusted to a pH of 1 with concentrated hydrochloric acid and the mixture was filtered to remove the precipitate formed. The filtrate was concentrated to dryness, and the residue was crystallized by adding acetone. An aqueous sodium hydroxide solution was then added to the crystals to a pH of 8. The precipitate formed was filtered and recrystallized from ethanol to obtain 1.3 g of a white amorphous material having a melting point of 147°–148° C (with foaming and decomposition). The material thus obtained was confirmed by NMR and IR spectral analyses and elemental analysis to be 5-[1-hydroxy-2-(2-phenethylamino)]butyl-8-hydroxycarbostyril (I) trihydrate.

EXAMPLE 13

2.5 g of chloranil and 20 ml of xylene were added to 2.2 g of 5-(1-hydroxy-2-isopropylamino)propyl-8-hydroxy-3,4-dihydrocarbostyril (VII), and the mixture was heated under refluxing for 24 hours. The reaction mixture was concentrated to dryness and the residue was washed thoroughly with 50 ml of carbon tetrachloride. The residue was then dissolved in 30 ml of methanol and hydrogen chloride gas was introduced into the solution to a pH of 1 followed by cooling. The precipitated crystals were filtered and recrystallized from methanol to obtain 1.5 g of a material having a melting point of 164°–166° C (with decomposition). The product thus obtained was confirmed by NMR and IR spectral analyses and elemental analysis to be 5-(1-hydroxy-2-isopropylamino)propyl-8-hydroxycarbostyril (I) hydrochloride monohydrate.

In the same manner as described in the above Example 13, the following compounds of the formula (I) was also prepared from the corresponding 3,4-dihydrocarbostyril compound of the formula (VII):

5-(1-Hydroxy-2-sec-butylamino)butyl-8-hydroxycarbostyril hydrochloride monohydrate having a melting point of 182°–183° C (with decomposition).

5-(1-Hydroxy-2-ethylamino)butyl-8-hydroxycarbostyril hydrochloride having a melting point of 174°–177.5° C (with decomposition).

EXAMPLE 14

10 ml of a 47% aqueous hydrobromic acid was added to 1 g of 5-(1-hydroxy-2-isopropylamino)propyl-8-methoxycarbostyril hydrochloride (VIII) monohydrate, and the mixture was heated under refluxing for 15 hours followed by concentration to dryness. Acetone was added to the resulting residue to crystallize the product which was then adjusted to a pH of 8 with dilute aqueous sodium hydroxide solution. The precipitated crystals were filtered, washed with water and dissolved in ethanol. The solution was adjusted to a pH 1 with concentrated hydrochloric acid and concentrated to dryness. The residue thus obtained was recrystallized from a mixture of ethanol and diethyl ether to obtain 0.7 g of a material having a melting point of ⅞°–166° C (with decomposition). The product thus obtained was confirmed by NMR and IR spectral analyses and elemental analysis to be 5-(1-hydroxy-2-isopropylamino)propyl-8-hydroxycarbostyril (I) hydrochloride.

In the same manner as described in Example 14, the following compound of the formula (I) was obtained from the corresponding 8-methoxy compound of the formula (VIII).

5-(1-Hydroxy-2-isopropylamino)butyl-8-hydroxycarbostyril hydrochloride having a melting point of 213°–214° C (with decomposition).

REFERENCE EXAMPLE

The stimulating activity of the compounds of this invention on $\beta$-adreno-receptor was determined as follows:

Male hybrid adult dogs, weighing 10 to 15 kg were anesthesized with 30 mg/kg of body weight of sodium pentobarbital administered intravenously. Each of the anesthesized dogs was secured on its back and a cannula was inserted into the trachea. Artificial respiration was conducted using a device according to the Konzett-Rössler method (Konzett H. & Rössler R., "Versuchsanordnug zu Untersuchungen an der Bronchial Moskolatur", *Arch. Exp. Path., Pharmack*, 195, 71 – 74, 27 – 40 (1940)). The volume of the overflowing air at the time of inhalation was measured through a pneumotachometer to determine the bronchial resistance and the values obtained were recorded on a polygraph.

In the above experiment, histamine was employed as a bronchoconstrictor at a dosage level of 10 mg/kg of body weight, and an aqueous solution containing each of the test compounds and controls shown in Table 1 below was then administered to each of the anesthesized dogs through the femoral vein at the various dosage levels as shown in Table 1 below 1 minute before the administration of the histamine. Sodium pentobarbital was infused during the experiment at a dosage level of 4 mg/kg of body weight/hr using an automatic injector in order to inhibit spontaneous respiration and to keep the anesthetic condition constant over the test period. The results obtained are shown in Table 1 below.

Table 1

| | Bronchial Resistance(%) | | | | | | | | |
|---|---|---|---|---|---|---|---|---|---|
| | Dosage Level ($\mu$g/Kg) | | | | | | | | |
| Compound | 0.01 | 0.03 | 0.1 | 0.3 | 1.0 | 3.0 | 10 | 30 | 100 |
| 5-(1-Hydroxy-2-isopropylamino)-butyl-8-hydroxy-carbostyril Hydrochloride | 0 | 11.1 | 30.5 | 63.3 | 87.3 | 100 | — | — | — |
| 5-(1-Hydroxy-2-isopropylamino)-propyl-8-hydroxy-carbostyril Hydrochloride (Control) | 0 | 5.5 | 28.3 | 65.8 | 89.4 | 100 | — | — | — |
| Isoproterenol | 0 | 16.6 | 58.3 | 83.3 | 100 | — | — | — | — |
| Salbutamol | 0 | 0 | 16.6 | 33.3 | 66.6 | 100 | — | — | — |

Table 1-continued

| Compound | Bronchial Resistance(%) Dosage Level (μg/Kg) | | | | | | | | |
|---|---|---|---|---|---|---|---|---|---|
| | 0.01 | 0.03 | 0.1 | 0.3 | 1.0 | 3.0 | 10 | 30 | 100 |
| Metaproterenol Sulfate (Arotec) | 0 | 0 | 2.7 | 11.1 | 27.5 | 50.0 | 88.3 | 100 | — |
| Quinterenol | 0 | 0 | 0 | 0 | 0 | 0 | 0 | 7.6 | 15.3 |

Further, the acute toxicity was determined with respect to a representative compound of the present invention, 5-(1-hydroxy-2-isopropylamino)butyl-8-hydroxycarbostyril hydrochloride, using 5 to 6 groups each containing 10 male rats (dd strain; body weight, 18 to 22 g) which had been fasted for 12 hours prior to the test. Salbutamol and isoproterenol were used as a control. The $LD_{50}$ (50% lethal dose) results are as follows.

Table 2

| Compound | $LD_{50}$ (mg/Kg) | |
|---|---|---|
| | i.v. | p.o. |
| 5-(1-Hydroxy-2-isopropylamino)-butyl-8-hydroxycarbostyril Hydrochloride (Control) | 80 (64–100) | 2600 (2207–3063) |
| Salbutamol | 57.1 (52.7–61.9) | 4620* (4160–5130)* 660 (412.5–1056) |
| Isoproterenol | 112.5 (87.9–144.0) | 2587* 355 (235.1–536.1) |

Note: *Literature values

The compounds of the present invention can be administered at a dosage level of from 100 to 50 mg/Kg/day by oral, intraveous, intramuscular, intrarectal or inhalation administration in a conventional pharmaceutical dosage form such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The composition may contain other active components which do not adversely affect the activities of the compounds of this invention.

Suitable pharmaceutical carriers or diluents include solid carriers such as corn starch, calcium sulfate dihydrate, magnesium stearate, lactose, Aerosil (tradename of Nihon Aerosil Co., Ltd., Japan) and the like which are suitable for use in oral, suppository, injectable and inhalent formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using physiologically acceptable carriers or diluents in the form of a solution, suspension or dry preparation which is reconstituted instantaneously with a vehicle for injection just before administration.

The compounds of the present invention are advantageously administered in the form of an aerosol spray formulation by inhalation.

Typical examples of suitable formulations are given below, but it is to be noted that other dosage forms can also be prepared using other compounds of thiis invention according to the well-established pharmaceutical techniques.

FORMULATION 1

Tablets each containing the following compounds were prepared from the following components:

| Component | Amount |
|---|---|
| 5-(1-Hydroxy-2-isopropylamino)-ethyl-8-hydroxycarbostyril | 1 mg |
| Corn Starch | 70 mg |
| Magnesium Stearate | 9 mg |
| Lactose | 20 mg |
| Total | 100 mg |

FORMULATION 2

Aerosol spray for inhalation containing the following components per each dose was prepared and filled in the aerosol dipenser:

| Component | Amount |
|---|---|
| 5-(1-Hydroxy-2-isopropylamino)-ethyl-8-hydroxycarbostyril | 50 mcg |
| Oleic Acid | 10 mcg |
| Dichlorodifluoromethane | 57 mg |
| Trichlorofluoromethane | 25 mg |

While the present invention has been described in detail with reference to specific embodiments thereof, it is apparent to one skilled in the art that various changes and modifications can be made therein without departing from the spirit and the scope of the present invention.

What is claimed is:

1. A 5-[1-hydroxy-2-(substituted-amino)]alkyl-8-hydroxy-carbostyril compound represented by the formula (I)

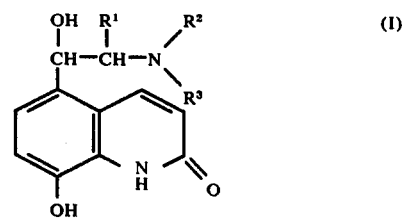

wherein $R^1$ represents an alkyl group having 1 to 4 carbon atoms and $R^2$ and $R^3$, which may be the same or different, each represents a hydrogen atom, an alkyl group having 1 to 4 carbon atoms, a phenylalkyl group having a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6- membered heterocyclic ring, substituted by an alkyl group having 1–4 carbon atoms or unsubstituted selected from the group consisting of pyrrolidino, piperidino, morpholino and piperazino and the pharmaceutically acceptable acid addition salts thereof.

2. A 5-[1-hydroxy-2-(substituted-amino)]alkyl-8-hydroxy-carbostyril compound represented by the formula (I)

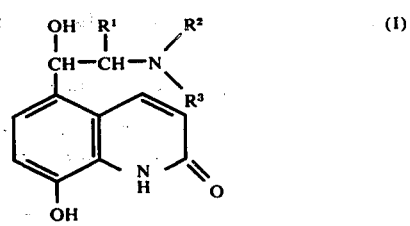

wherein $R^1$ represents an alkyl group having 1 to 4 carbon atoms and $R^2$ and $R^3$, which may be the same or different, each represents a hydrogen atom, an alkyl group having 1 to 4 carbon atoms, a phenylalkyl group having a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a heterocyclic ring which is unsubstituted or substituted by an alkyl group having 1–4 carbon atoms, said heterocyclic ring being selected from the group consisting of piperidino and pyrrolidino, and the pharmaceutically acceptable acid addition salts thereof.

3. 5-(1-Hydroxy-2-isopropylamino)butyl-8-hydroxycarbostyril according to claim 2.

4. 5-(1-Hydroxy-2-sec-butylamino)butyl-8-hydroxycarbostyril according to claim 2.

5. 5-(1-Hydroxy-2-ethylamino)butyl-8-hydroxycarbostyril according to claim 2.

6. 5-[1-Hydroxy-2-(2-phenethylamino)]butyl-8-hydroxycarbostyril according to claim 2.

7. 5-(1-Hydroxy-2-isopropylamino)propyl-8-hydroxycarbostyril according to claim 2.

8. 5-(1-Hydroxy-2-tert-butylamino)propyl-8-hydroxycarbostyril according to claim 2.

* * * * *